US010048750B2

(12) United States Patent
Du et al.

(10) Patent No.: US 10,048,750 B2
(45) Date of Patent: Aug. 14, 2018

(54) CONTENT PROJECTION SYSTEM AND CONTENT PROJECTION METHOD

(71) Applicant: Beijing Zhigu Rui Tuo Tech Co., Ltd, Beijing (CN)

(72) Inventors: Lin Du, Beijing (CN); Hongjiang Zhang, Beijing (CN)

(73) Assignee: BEIJING ZHIGU RUI TUO TECH CO., LTD, Beijing (CN)

( * ) Notice: Subject to any disclaimer, the term of this patent is extended or adjusted under 35 U.S.C. 154(b) by 35 days.

(21) Appl. No.: 14/783,503

(22) PCT Filed: Dec. 4, 2013

(86) PCT No.: PCT/CN2013/088554
§ 371 (c)(1),
(2) Date: Oct. 9, 2015

(87) PCT Pub. No.: WO2015/027599
PCT Pub. Date: Mar. 5, 2015

(65) Prior Publication Data
US 2016/0179193 A1 Jun. 23, 2016

(30) Foreign Application Priority Data
Aug. 30, 2013 (CN) .......................... 2013 1 0390652

(51) Int. Cl.
G06T 19/00 (2011.01)
G06F 3/01 (2006.01)
(Continued)

(52) U.S. Cl.
CPC .............. G06F 3/013 (2013.01); A61B 3/113 (2013.01); G02B 27/017 (2013.01);
(Continued)

(58) Field of Classification Search
None
See application file for complete search history.

(56) References Cited

U.S. PATENT DOCUMENTS 4,264,154 A   4/1981 Petersen
4,572,616 A   2/1986 Kowel et al.
(Continued)

FOREIGN PATENT DOCUMENTS

CN   1372650   10/2002
CN   1470227   1/2004
(Continued)

OTHER PUBLICATIONS

Gao et al., "Measuring Directionality of the Retinal Reflection with a Shack-Hartmann Wavefront Sensor," 2009, Optical Society of America.*
(Continued)

Primary Examiner — Nicholas R Wilson
(74) Attorney, Agent, or Firm — Amin, Turocy & Watson, LLP

(57) ABSTRACT

This application discloses a content projection system and a content projection method. The system comprises: a gaze point detection apparatus, configured to detect a gaze point location of an eye; an image generating apparatus, configured to generate a virtual image according to visual information and the gaze point location; and a virtual image projection apparatus, configured to project the virtual image to the fundus according to the gaze point location. According to the system and method in the embodiments of the present application, the gaze point location of a user is detected in real time, an imaging parameter corresponding to the visual information is obtained with respect to the gaze point location, and therefore, the virtual image is generated and projected to the fundus, so that virtual graphic information (Continued)

is better fused with reality information, and the user obtains a better sense of immersion.

36 Claims, 8 Drawing Sheets

(51) Int. Cl.
 A61B 3/113 (2006.01)
 G02B 27/01 (2006.01)
 G02B 27/00 (2006.01)
(52) U.S. Cl.
 CPC ........ G06T 19/006 (2013.01); *G02B 27/0093* (2013.01); *G02B 2027/014* (2013.01); *G02B 2027/0127* (2013.01); *G02B 2027/0134* (2013.01); *G02B 2027/0138* (2013.01); *G02B 2027/0187* (2013.01)

(56) References Cited

U.S. PATENT DOCUMENTS

| | | |
|---|---|---|
| 5,182,585 A | 1/1993 | Stoner |
| 5,537,163 A | 7/1996 | Ueno |
| 6,072,443 A | 6/2000 | Nasserbakht et al. |
| 6,111,597 A | 8/2000 | Tabata |
| 6,151,061 A | 11/2000 | Tokuhashi |
| 6,152,563 A | 11/2000 | Hutchison et al. |
| 6,325,513 B1 | 12/2001 | Bergner et al. |
| 7,001,020 B2 | 2/2006 | Yancey et al. |
| 7,298,414 B2 | 11/2007 | Stavely et al. |
| 7,334,892 B2 | 2/2008 | Goodall et al. |
| 7,486,988 B2 | 2/2009 | Goodall et al. |
| 7,764,433 B2 | 7/2010 | Kam et al. |
| 7,766,479 B2 | 8/2010 | Ebisawa |
| 8,104,892 B2 | 1/2012 | Hillis et al. |
| 8,109,632 B2 | 2/2012 | Hillis et al. |
| 8,282,212 B2 | 10/2012 | Hillis et al. |
| 8,384,999 B1 | 2/2013 | Crosby et al. |
| 8,896,632 B2 | 11/2014 | MacDougall et al. |
| 2002/0101568 A1* | 8/2002 | Eberl .................. G02B 27/017 351/211 |
| 2002/0113943 A1 | 8/2002 | Trajkovic et al. |
| 2003/0043303 A1 | 3/2003 | Karuta et al. |
| 2003/0125638 A1 | 7/2003 | Husar et al. |
| 2005/0003043 A1 | 1/2005 | Sewal et al. |
| 2005/0014092 A1 | 1/2005 | Hasegawa et al. |
| 2005/0030438 A1 | 2/2005 | Nishioka |
| 2006/0016459 A1 | 1/2006 | Mcfarlane et al. |
| 2006/0103808 A1 | 5/2006 | Horie |
| 2006/0122530 A1 | 6/2006 | Goodall et al. |
| 2006/0146281 A1 | 7/2006 | Goodall et al. |
| 2006/0164593 A1 | 7/2006 | Peyghambarian et al. |
| 2006/0122531 A1 | 8/2006 | Goodall et al. |
| 2007/0019157 A1 | 1/2007 | Hills et al. |
| 2007/0211207 A1 | 9/2007 | Lo et al. |
| 2008/0002262 A1* | 1/2008 | Chirieleison ...... G02B 27/0093 359/630 |
| 2008/0106633 A1 | 5/2008 | Blum et al. |
| 2009/0066915 A1 | 3/2009 | Lai |
| 2009/0189974 A1 | 7/2009 | Deering |
| 2009/0279046 A1 | 11/2009 | Dreher et al. |
| 2009/0303212 A1 | 12/2009 | Akutsu et al. |
| 2011/0018903 A1 | 1/2011 | Lapstun et al. |
| 2011/0019258 A1 | 1/2011 | Levola |
| 2011/0213462 A1 | 1/2011 | Holladay |
| 2011/0051087 A1 | 3/2011 | Inoue et al. |
| 2011/0242277 A1 | 10/2011 | Do et al. |
| 2011/0279277 A1 | 11/2011 | Li-Chung |
| 2012/0007959 A1 | 1/2012 | Kwon et al. |
| 2012/0013389 A1 | 1/2012 | Thomas et al. |
| 2012/0038549 A1 | 2/2012 | Mandella et al. |
| 2012/0092618 A1 | 4/2012 | Yoo et al. |
| 2012/0113235 A1 | 5/2012 | Shintani |
| 2012/0127062 A1 | 5/2012 | Bar-Zeev et al. |
| 2012/0127422 A1 | 5/2012 | Tian et al. |
| 2012/0133891 A1 | 5/2012 | Jiang |
| 2012/0140044 A1 | 6/2012 | Galstian et al. |
| 2012/0154277 A1 | 6/2012 | Bar-Zeev et al. |
| 2012/0169730 A1 | 7/2012 | Inoue |
| 2012/0206485 A1 | 8/2012 | Osterhout et al. |
| 2012/0212499 A1 | 8/2012 | Haddick et al. |
| 2012/0212508 A1 | 8/2012 | Kimball |
| 2012/0242698 A1 | 9/2012 | Haddick et al. |
| 2012/0290401 A1 | 11/2012 | Neven |
| 2012/0293773 A1 | 11/2012 | Publicover et al. |
| 2012/0307208 A1 | 12/2012 | Trousdale |
| 2013/0044042 A1 | 2/2013 | Olsson et al. |
| 2013/0050646 A1 | 2/2013 | Nanbara |
| 2013/0072828 A1 | 3/2013 | Sweis et al. |
| 2013/0107066 A1 | 5/2013 | Venkatraman et al. |
| 2013/0127980 A1 | 5/2013 | Haddick et al. |
| 2013/0135203 A1 | 5/2013 | Croughwell |
| 2013/0147836 A1 | 6/2013 | Small et al. |
| 2013/0215504 A1 | 8/2013 | Kim et al. |
| 2013/0241805 A1 | 9/2013 | Gomez |
| 2013/0241927 A1 | 9/2013 | Vardi |
| 2013/0278631 A1 | 10/2013 | Border et al. |
| 2013/0335301 A1 | 12/2013 | Wong et al. |
| 2013/0335404 A1* | 12/2013 | Westerinen ............. G06F 3/033 345/419 |
| 2013/0342572 A1 | 12/2013 | Poulos et al. |
| 2014/0078175 A1 | 3/2014 | Forutanpour et al. |
| 2014/0160157 A1 | 6/2014 | Poulos et al. |
| 2014/0225915 A1 | 8/2014 | Theimer et al. |
| 2014/0225918 A1 | 8/2014 | Mittal et al. |
| 2014/0232746 A1 | 8/2014 | Ro et al. |
| 2014/0240351 A1 | 8/2014 | Scavezze et al. |
| 2014/0267400 A1 | 9/2014 | Mabbutt et al. |
| 2014/0267420 A1 | 9/2014 | Schowengerdt et al. |
| 2014/0282224 A1 | 9/2014 | Pedley |
| 2014/0327875 A1 | 11/2014 | Blum et al. |
| 2014/0375680 A1 | 12/2014 | Ackerman et al. |
| 2015/0002542 A1 | 1/2015 | Chan et al. |
| 2015/0035861 A1 | 2/2015 | Salter et al. |
| 2015/0234184 A1 | 8/2015 | Schowengerdt et al. |
| 2015/0235632 A1 | 8/2015 | Liu et al. |
| 2015/0070391 A1 | 9/2015 | Nishimaki et al. |
| 2016/0034032 A1 | 2/2016 | Jeong |
| 2016/0035139 A1 | 2/2016 | Fuchs et al. |
| 2016/0062454 A1 | 3/2016 | Wang et al. |
| 2016/0171772 A1 | 6/2016 | Ryznar et al. |
| 2016/0189432 A1 | 6/2016 | Bar-Zeev et al. |
| 2016/0196603 A1 | 7/2016 | Perez et al. |
| 2016/0299360 A1 | 10/2016 | Fonte et al. |
| 2016/0370605 A1 | 12/2016 | Ain-Kedem |
| 2017/0092235 A1 | 3/2017 | Osman et al. |

FOREIGN PATENT DOCUMENTS

| | | |
|---|---|---|
| CN | 1141602 | 3/2004 |
| CN | 1527126 | 9/2004 |
| CN | 1604014 A | 4/2005 |
| CN | 1645244 | 7/2005 |
| CN | 1653374 | 8/2005 |
| CN | 1901833 | 1/2007 |
| CN | 1912672 | 2/2007 |
| CN | 2868183 | 2/2007 |
| CN | 1951314 | 4/2007 |
| CN | 101069106 | 11/2007 |
| CN | 101072534 | 11/2007 |
| CN | 101097293 | 1/2008 |
| CN | 101103902 | 1/2008 |
| CN | 201005945 | 1/2008 |
| CN | 101116609 | 2/2008 |
| CN | 101155258 | 4/2008 |
| CN | 101194198 | 6/2008 |
| CN | 101430429 | 5/2009 |
| CN | 201360319 | 9/2009 |
| CN | 201352278 | 11/2009 |
| CN | 101900927 | 1/2010 |
| CN | 101662696 | 3/2010 |
| CN | 201464738 | 5/2010 |
| CN | 101782685 | 7/2010 |

(56) References Cited

FOREIGN PATENT DOCUMENTS

| | | |
|---|---|---|
| CN | 101819331 | 9/2010 |
| CN | 101819334 | 9/2010 |
| CN | 201637953 | 11/2010 |
| CN | 101917638 | 12/2010 |
| CN | 201754203 | 3/2011 |
| CN | 102008288 | 4/2011 |
| CN | 102083390 | 6/2011 |
| CN | 102203850 | 9/2011 |
| CN | 102292017 | 12/2011 |
| CN | 102419631 A | 4/2012 |
| CN | 102481097 | 5/2012 |
| CN | 101149254 | 6/2012 |
| CN | 102487393 | 6/2012 |
| CN | 202267785 | 6/2012 |
| CN | 102572483 | 7/2012 |
| CN | 102576154 | 7/2012 |
| CN | 202383380 | 8/2012 |
| CN | 102918444 A | 2/2013 |
| CN | 102939557 | 2/2013 |
| CN | 102981270 | 3/2013 |
| CN | 103054695 | 4/2013 |
| CN | 103065605 | 4/2013 |
| CN | 103150013 | 6/2013 |
| CN | 103190883 | 7/2013 |
| CN | 103197757 A | 7/2013 |
| CN | 103280175 | 9/2013 |
| CN | 103297735 | 9/2013 |
| CN | 103353663 | 10/2013 |
| CN | 103353667 | 10/2013 |
| CN | 103353677 | 10/2013 |
| CN | 103558909 | 2/2014 |
| DE | 19959379 | 7/2000 |
| EP | 2646859 | 10/2013 |
| JP | 03023431 | 1/1991 |
| JP | 2676870 | 11/1997 |
| JP | -109289973 | 11/1997 |
| JP | 3383228 B2 | 3/2003 |
| JP | 2003307466 | 10/2003 |
| JP | 2005058399 | 3/2005 |
| JP | 2007129587 | 5/2007 |
| JP | 201143876 | 3/2011 |
| JP | 2012199621 | 10/2012 |
| JP | 2012247449 | 12/2012 |
| TW | 201012448 | 4/2010 |
| WO | 2004023167 | 3/2004 |
| WO | 2005077258 A1 | 8/2005 |
| WO | 2012075218 | 6/2012 |
| WO | 2012083415 A1 | 6/2012 |
| WO | 2013074851 | 5/2013 |

OTHER PUBLICATIONS

Lee et al., "A robust eye gaze tracking method based on a virtual eyeball model," Springer-Verlag, 2008.*
International Search Report dated Mar. 6, 2014 for PCT Application No. PCT/CN2013/088540, 8 pages.
Jeong, et al. "Tunable microdoublet lens array", Optics Express, vol. 12, Issue 11, May 2004, pp. 2494-2500.
International Search Report dated Apr. 3, 2014 for PCT Application No. PCT/CN2013/088531, 10 pages.
International Search Report dated Feb. 27, 2014 for PCT Application No. PCT/CN2013/088522, 6 pages.
International Search Report dated May 8, 2014 for PCT Application No. PCT/CN2013/088547, 4 pages.
Kim et al., "A 200 s Processing Time Smart Image Sensor for an Eye Tracker using pixel-level analog image processing", IEEE Journal of Solid-State Circuits, vol. 44, No. 9, Sep. 2009, 10 pages.
Hansen et al., "In the eye of the beholder: a survey of models for eyes and gaze", IEEE Transactions on pattern analysis and machine intelligence, vol. 32, No. 3, Mar. 2010, 23 pages.
International Search Report dated May 28, 2014 for PCT Application No. PCT/CN2013/088553, 6 pages.
International Search Report dated May 28, 2014 for PCT Application No. PCT/CN2013/088545, 4 pages.
Office Action dated Feb. 27, 2017 for U.S. Appl. No. 14/783,495, 39 pages.
Office Action dated Apr. 21, 2017 for U.S. Appl. No. 14/781,581, 19 pages.
Office Action dated Apr. 20, 2017 for U.S. Appl. No. 14/781,578, 77 pages.
Office Action dated Mar. 30, 2017 for U.S. Appl. No. 15/028,019, 36 pages.
Office Action dated May 3, 2017 for U.S. Appl. No. 14/781,306, 46 pages.
International Search report dated Jun. 12, 2014 for PCT Application No. PCT/CN2013/088554, 4 pages.
Ji et al., "Real-Time Eye, Gaze and Face Pose Tracking for Monitoring Driver Vigilance", Real-Time Imaging 8, 357-377 (2002) available online at http://www.idealibrary.com, 21 pages.
International Search Report dated Jan. 8, 2015 for PCT Application No. PCT/CN2014/088242, 2 pages.
International Search Report dated May 5, 2014 for PCT Application No. PCT/CN2013/088544, 4 pages.
International Search Report dated Jun. 5, 2014 for PCT Application No. PCT/CN2013/088549, 4 pages.
Smith, et al., "Determining Driver Visual Attention With One Camera", IEEE Transactions on Intelligent Transportation Systems, vol. 4, No. 4, Dec. 2003, 14 Pages.
Singh, et al., "Human Eye Tracking and Related Issues: A Review", International Journal of Scientific and Research Publications, vol. 2, Issue 9, Sep. 2012, ISSN 2250-3153, 9 pages.
Office Action dated Dec. 29, 2016 for U.S. Appl. No. 14/780,519, 25 pages.
Office Action dated Jun. 29, 2017 for U.S. Appl. No. 14/783,495, 50 pages.
Office Action dated Jul. 12, 2017 for U.S. Appl. No. 14/780,519, 45 pages.
Office Action dated Jun. 8, 2017 for U.S. Appl. No. 14/779, 968, 79 pages.
Office Action dated Oct. 4, 2017 for U.S. Appl. No. 14/781,584, 95 pages.
Office Action dated Nov. 9, 2017 for U.S. Appl. No. 14/781,578, 64 pages.
Office Action dated Nov. 9, 2017 for U.S. Appl. No. 14/780,519, 24 pages.
Office Action dated Nov. 17, 2017 for U.S. Appl. No. 14/783,495, 32 pages.
Office Action dated Dec. 14, 2017 for U.S. Appl. No. 14/779,321, 82 pages.
Office Action dated Dec. 15, 2017 for U.S. Appl. No. 14/779,968, 67 pages.
Office Action dated Feb. 5, 2018 for U.S. Appl. No. 14/779,321, 38 pages.
Office Action dated Jun. 29, 2018 for U.S. Appl. No. 14/781,578, 67 pages.
Office Action dated Jun. 25, 2018 for U.S. Appl. No. 14/779,321, 43 pages.
Office Action dated Jun. 14, 2018 for U.S. Appl. No. 14/780,519, 29 pages.

* cited by examiner

CONTENT PROJECTION SYSTEM AND CONTENT PROJECTION METHOD

RELATED APPLICATION

The present application is a U.S. National Stage filing under 35 U.S.C. § 371 of international patent cooperation treaty (PCT) application No. PCT/CN2013/088554, filed Dec. 4, 2013, and entitled "CONTENT PROJECTION SYSTEM AND CONTENT PROJECTION METHOD," which claims priority to Chinese Patent Application No. 201310390652.6, entitled "CONTENT PROJECTION SYSTEM AND METHOD", filed on Aug. 30, 2013, which applications are hereby incorporated herein by reference in their respective entireties.

TECHNICAL FIELD

The present application relates to the field of virtual reality technologies, and in particular, to a content projection system and method.

BACKGROUND

In a mixed reality environment, a system often displays virtual graphical information, but currently, fused display of virtual graphic information and reality information is not yet implemented desirably. For example, when a user gazes somewhere (an actual object or a virtual graph), due to an incorrect depth or location of a virtual graph, the user fails to clearly see virtual graphic information needing to be seen; or, when a user gazes somewhere, virtual graphic information located at other depths and locations is also clearly displayed, and no proper bokeh effect is produced, which affects a real sense of immersion of the user. For example, currently, Google glasses can only display virtual content on a virtual screen at a specific distance, and as a result, the content cannot be well fused with the reality; therefore, the virtual screen can only be placed in angled upper front of the glasses, and a user needs to deliberately look upwards to view virtual graphic information, which seriously affects visual experience of the user. However, in a mixed reality system with stereoscopic visions for both eyes, information of stereoscopic depth is further added, and consequently, it is harder to reconcile a virtual system and a reality system, and setting the location of the virtual graphic information incorrectly further causes trouble such as diminution of vision, dizziness, and headache to a user.

SUMMARY

The following presents a simplified summary in order to provide a basic understanding of some example embodiments disclosed herein. This summary is not an extensive overview. It is intended to neither identify key or critical elements nor delineate the scope of the example embodiments disclosed. Its sole purpose is to present some concepts in a simplified form as a prelude to the more detailed description that is presented later.

An example objective of the present application is to provide a content projection system and method, so that virtual graphic information is better fused with reality information, thereby improving visual experience of a user.

To achieve the foregoing objective, in a first example embodiment, this application provides a content projection system, comprising:

a gaze point detection apparatus, configured to detect a current gaze point location of an eye of a user;

an image generating apparatus, configured to generate a virtual image according to visual information and the gaze point location; and a virtual image projection apparatus, configured to project the virtual image to the fundus of the eye according to the gaze point location.

In a second example embodiment, the present application further provides a content projection method, comprising:

a gaze point detection step, for detecting a current gaze point location of an eye of a user;

an image generating step, for generating a virtual image according to visual information and the gaze point location; and a virtual image projection step, for projecting the virtual image to the fundus of the eye according to the gaze point location.

According to the system and method in the embodiments of the present application, a gaze point location of a user is detected in real time, an imaging parameter corresponding to visual information is obtained with respect to the gaze point location, and therefore, a virtual image is generated and projected to the fundus, so that virtual graphic information is better fused with reality information, the user obtains a better sense of immersion, and visual experience of the user is improved.

DETAILED DESCRIPTION

The method and apparatus of the present application are described below in detail with reference to the accompanying drawings and the embodiments.

Figure 1:
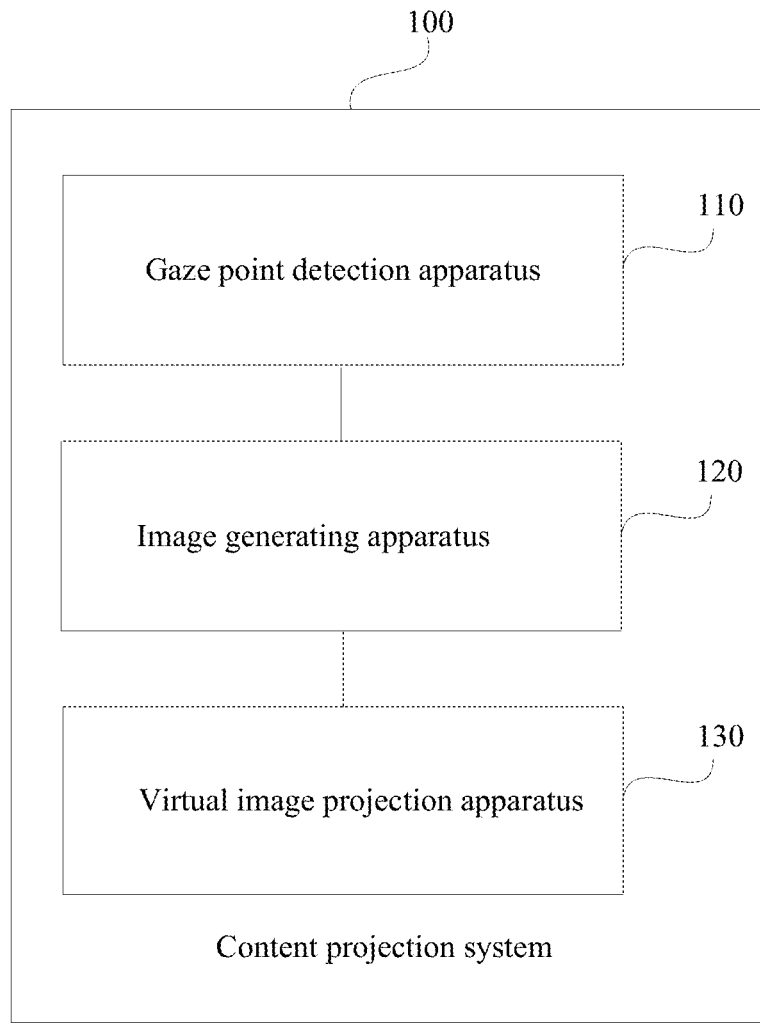
FIG. 1 is a schematic structural block diagram of a content projection system according to an embodiment of the present application.

In occasions of virtual reality, mixed reality, enhanced reality, enhanced virtuality, and the like in which virtual images need to be projected, to obtain a better fusion effect between a real scenario and a virtual scenario, or between virtual scenarios, and to bring a better sense of immersion to a user, a virtual image needing to be projected needs to be formed at a current gaze point location of the user. Therefore, as shown in FIG. 1, an embodiment of the present application provides a content projection system 100, comprising:

a gaze point detection apparatus 110, configured to detect a current gaze point location of an eye;

an image generating apparatus 120, configured to generate a virtual image according to visual information and the gaze point location; and a virtual image projection apparatus 130, configured to project the virtual image to the fundus according to the gaze point location.

In the embodiment of the present application, a gaze point location is detected in real time, and a corresponding virtual image is generated according to the current gaze point location, so that a virtual image viewed by a user changes as the gaze point changes, the virtual image is better fused with a current real scenario or virtual scenario, and the user has a more real feeling, which brings a better sense of immersion.

In a possible implementation manner of the embodiment of the present application, the content projection system 100 may be a portable and easy-to-use apparatus such as a pair of glasses (comprising frame glasses, contact lenses, goggles, and the like) having a gaze point detection apparatus 110 and a virtual image projection apparatus 130. In particular, for a user who originally has an eye disease such as a refractive error and needs to wear glasses for refractive correction, the system of the present application may be directly implemented on the glasses for refractive correction; or if a corresponding virtual scenario needs to be presented when a user watches a film or plays a game, the functions of the system may further be integrated on a device such as 3D glasses used when the user watches a film or plays a game, which brings no extra burden to the user.

Definitely, in other possible implementation manners of the embodiment of the present application, the content projection system may further be: for example, other optical devices used in coordination with eyes of the user, such as helmet eye lenses and a front windshield for driving.

Figure 2:
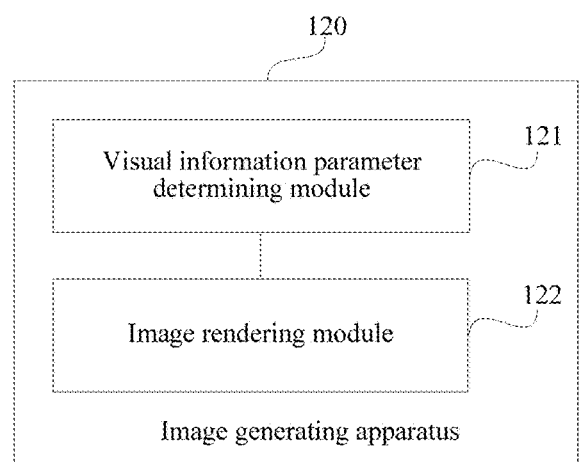
FIG. 2 is a schematic structural block diagram of an image generating apparatus of a content projection system according to an embodiment of the present application.

As shown in FIG. 2, in a possible implementation manner of an embodiment of the present application, the image generating apparatus 120 comprises:

a visual information parameter determining module 121, configured to determine an imaging parameter of the visual information according to the gaze point location; and an image rendering module 122, configured to generate, by means of rendering, the virtual image according to the visual information and the imaging parameter of the visual information.

The visual information described herein may be virtual graphic information (for example, a virtual dialog box and a virtual ball), image information (for example, picture or video information made in advance), or comprise both the graphic information and the image information.

The imaging parameter of the visual information described herein comprises: a location at which the visual information should be presented, a parameter of the visual information such as the size of the visual information, and a rendering parameter of the visual information, for example, a parameter of a virtual camera (such as a location, an orientation, and an angle of view), and a parameter such as light and special effects.

When a user views real objects with eyes, usually, the user can only clearly see objects within a certain range of depth of field near a gaze point, while a vague image of objects out of this range is formed at the fundus because these objects are out of focus. In a possible implementation manner of the embodiment of the present application, to make a generated virtual image better conform to visual effects of human eyes, and to bring more real experience to a user, the imaging parameter of the visual information further comprises depth-of-field information. The depth-of-field information may be used as a depth-of-field parameter of the virtual camera.

Therefore, in a possible implementation manner of the embodiment of the present application, the gaze point detection apparatus further comprises:

a pupil detection module, configured to detect a current size of the pupil of the eye.

A picture of the pupil is usually obtained by using an image collection module (such as a micro camera) capable of shooting an image of the surface of the eye, and then, the size of the pupil of the eye is calculated by means of image processing. The technology for detecting the size of an eye pupil is an existing technology, and is not described in this embodiment again.

In this implementation manner, the visual information parameter determining module generates the depth-of-field information according to the size of the pupil of the eye.

Obtaining depth-of-field information according to the size of an eye pupil is an existing technology, and is not further described in this embodiment again. Generally speaking, a larger pupil indicates a smaller depth of field, and a smaller pupil indicates a greater depth of field.

In a possible implementation manner of the embodiment of the present application, the image rendering module comprises:

a bokeh processing unit, configured to perform corresponding bokeh imaging processing on the visual information according to the imaging parameter of the visual information (which is mainly the foregoing depth-of-field information).

Herein, after the bokeh imaging processing is performed on the visual information according to the depth-of-field information, visual information out of the range of the depth of field is blurred, bringing real visual experience to a user.

Figure 3:
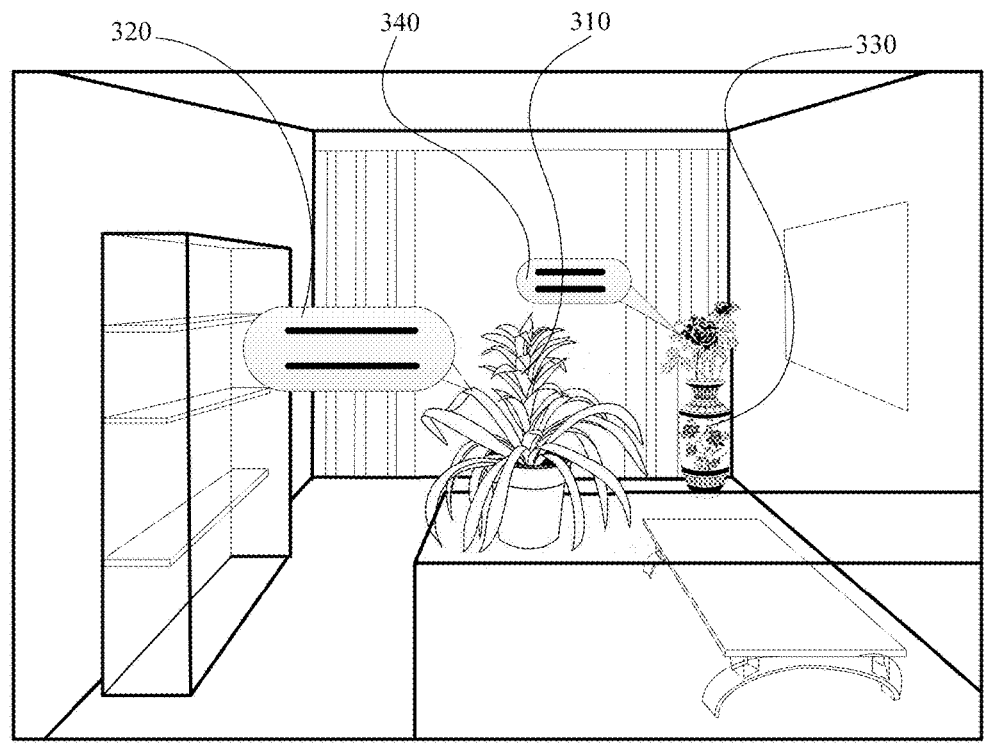
FIG. 3 is a diagram of a virtual-reality mixed scenario obtained by a user by using a content projection system according to an embodiment of the present application.

As shown in FIG. 3, in a possible implementation manner of the embodiment of the present application, a system of the embodiment of the present application needs to display, in a real scenario, virtual information corresponding to an object in the real scenario. When a gaze point of a user is at a flowerpot 310 nearby, visual information thereof needing to be correspondingly presented (in this implementation manner, the visual information is virtual graphic information) is first virtual information 320; when a gaze point of the user is at a vase 330 a little farther away, virtual graphic information thereof needing to be correspondingly presented is second virtual information 340.

Taking the gaze point of the user being at the flowerpot 310 as an example, the gaze point detection apparatus of the content projection system according to the embodiment of the present application detects that a current gaze point of an eye is at the flowerpot 310.

The image generating apparatus generates a corresponding virtual image according to the first virtual information 320, the second virtual information 340, and locations (separately near the flowerpot 310 and the vase 330) at which the first virtual information 320 and the second virtual information 340 need to be presented. For example, in this implementation manner, the virtual image is an image comprising the first virtual information 320 and the second virtual information 340 which are located at specific locations and have corresponding sizes (for example, an object farther away is smaller than it is at a near place). If the virtual image is further required to have an out-of-focus imaging effect corresponding to the eye, processing such as bokeh may further be performed on the second virtual information 340 according to current depth-of-field information of the eye, and then the second virtual information 340 and the first virtual information 320 together form the virtual image.

Finally, the virtual image projection apparatus projects the virtual image at the fundus, so that the eye views an image in which the virtual image and the real scenario are mixed, as shown in FIG. 3.

Figure 4:
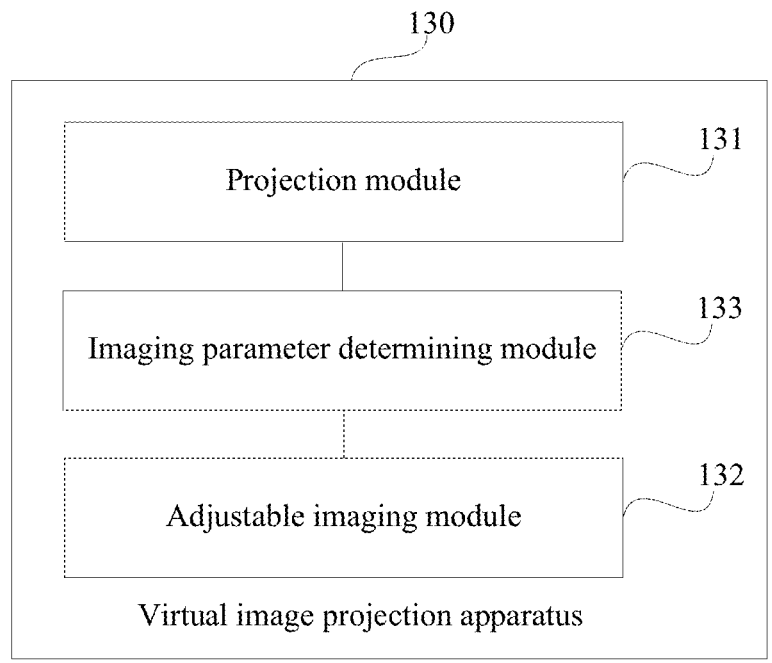
FIG. 4 is a schematic structural block diagram of a virtual image projection apparatus of a content projection system according to an embodiment of the present application.

As shown in FIG. 4, in a possible implementation manner of an embodiment of the present application, the virtual image projection apparatus 130 comprises:
  a projection module 31, configured to project the virtual image to the corresponding fundus;
  an adjustable imaging module 132, located on an optical path between the projection module and the fundus, and configured to form an image of the projected virtual image at the fundus; and
  an imaging parameter determining module 133, configured to determine at least one projection imaging parameter of the adjustable imaging module according to the gaze point location.

In this implementation manner, the projection module 131 may be a micro projector; and
  the imaging parameter generating module 133 generates the at least one projection imaging parameter of the adjustable imaging module 132 according to the gaze point location (the at least one projection imaging parameter herein refers to at least one imaging parameter used by the adjustable imaging module 132 to project the virtual image), and adjusts the adjustable imaging module 132 according to the at least one projection imaging parameter, so that the image of the projected virtual image can be clearly formed at the fundus, and a user can view the virtual image needing to be displayed.

The at least one projection imaging parameter of the adjustable imaging module 132 described herein comprises: a focal length of the adjustable imaging module 132, a location of the adjustable imaging module 132 on the optical path, and the like. The adjustable imaging module 132 may change a light transmission manner by changing a structure or a location of the adjustable imaging module 132; and the adjustable imaging module 132 may be formed by a single lens with an adjustable imaging parameter, or formed by a lens assembly formed by multiple lenses, or may be an optical system comprising lenses and other optical components.

Preferably, in a possible implementation manner of the embodiment of the present application, the adjustable imaging module 132 may comprise an electronic adjustable lens, such as a liquid or liquid crystal lens disclosed in the U.S. Patent Publication No. US20070211207A1 and U.S. Pat. No. 4,572,616A; by controlling liquid or liquid crystal in the lens, an imaging parameter such as a shape and a refractive index of the lens is changed quickly. If the system of the present application is applied to a portable and wearable device such as glasses, using a single electronic adjustable lens as the adjustable lens module 132 can make the system smaller, lighter, and portable; moreover, a manner of applying the electronic adjustable lens to glasses has commercial applications, such as the Empower electronic varifocal glasses launched by Pixeloptics.

In addition to the foregoing electronic adjustable lens, a lens assembly formed by multiple lenses may further be used to form the adjustable lens module 132. For example, the imaging parameter of the adjustable lens module 132 is adjusted by changing locations of the multiple lenses and angles of optical axes of the lenses, and eccentrically setting the optical axes of the multiple lenses, where a part of or all of the multiple lenses are adjustable lenses.

In a possible implementation manner of the embodiment of the present application, the adjustable image module further comprises:
  a beam splitting unit, configured to perform optical path transmission between the projection module and the fundus.

With the beam splitting unit, when viewing a real object or a virtual scenario in front, the user is not disturbed by the projection of the virtual image to the fundus of the eye of the user.

In the embodiment of the present application, the gaze point detection apparatus 110 may be in one of the following forms:
  a) a pupil direction detector is used to detect an optical axis direction of an eye, and then, a depth sensor (such as infrared distance measurement instrument) is used to obtain the depth of a gaze scenario of the eye, so as to obtain a gaze point location of a sight line of the eye; this technology is an existing technology, and is not described in this implementation manner again;
  b) optical axis directions of two eyes are separately detected, and then, an intersection of the optical axis directions of the two eyes is obtained, so as to obtain a gaze point location of a sight line of the eye; this technology is an existing technology, and is not described herein again; and
  c) a gaze point location of a sight line of an eye is obtained according to an optical parameter of an optical path between an image collection device and the eye when a clearest image presented on an imaging plane of the eye is collected. In this implementation manner, the gaze point detection apparatus 110 may be one of the gaze point detection apparatuses shown in the following FIG. 5a to FIG. 5f, FIG. 6, and FIG. 7.

Definitely, persons skilled in the art may know that, in addition to the gaze point detection apparatuses 110 in the foregoing forms, other apparatuses that can be used for detecting a gaze point of an eye of a user may also be applied in the system of the embodiment of the present application.

Figure 5A:
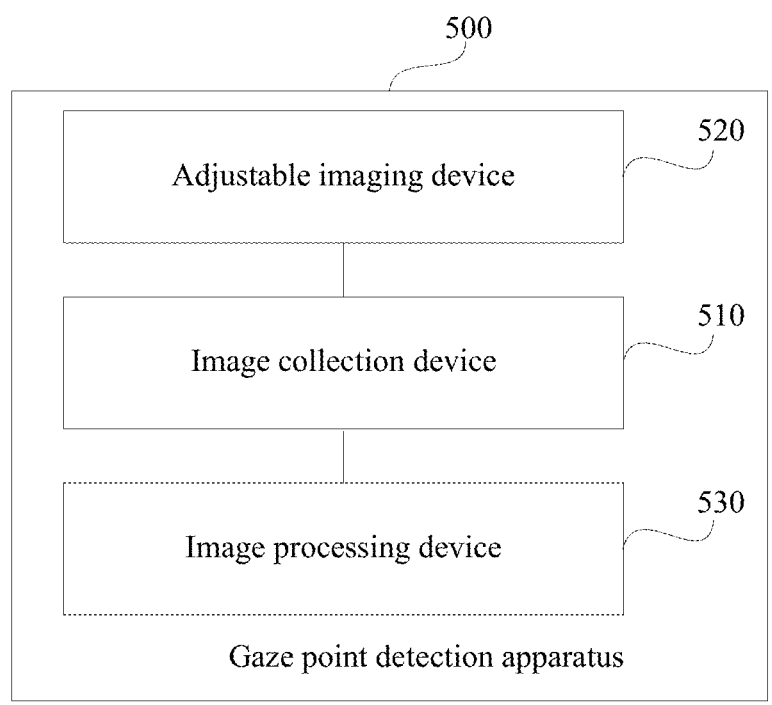
FIG. 5a is a structural block diagram of a gaze point detection apparatus of a content projection system according to an embodiment of the present application.

As shown in FIG. 5a, in a possible implementation manner of the embodiment of the present application, the gaze point detection apparatus 500 comprises:
- an image collection device 510, configured to collect an image presented at the fundus of the eye;
- an adjustable imaging device 520, configured to adjust an imaging parameter of an optical path between the image collection device and the eye, so that the image collection device obtains a clearest image; and
- an image processing device 530, configured to process the image obtained by the image collection device, and calculate the gaze point location of the eye according to the imaging parameter of the optical path between the image collection device and the eye when the clearest image is obtained and an optical parameter of the eye.

The gaze point detection apparatus 500 obtains, by analyzing and processing the image at the fundus of the eye, an optical parameter of the eye when the image collection device obtains the clearest image, and the current gaze point location of the eye can be calculated, which provides a basis for further eye self-adaptive operations.

The image presented at the "fundus" herein is mainly an image presented on the retina, and may be an image of the fundus, or an image of another object projected to the fundus. The eye herein may be a human eye, and may also be an eye of another animal.

Figure 5B:
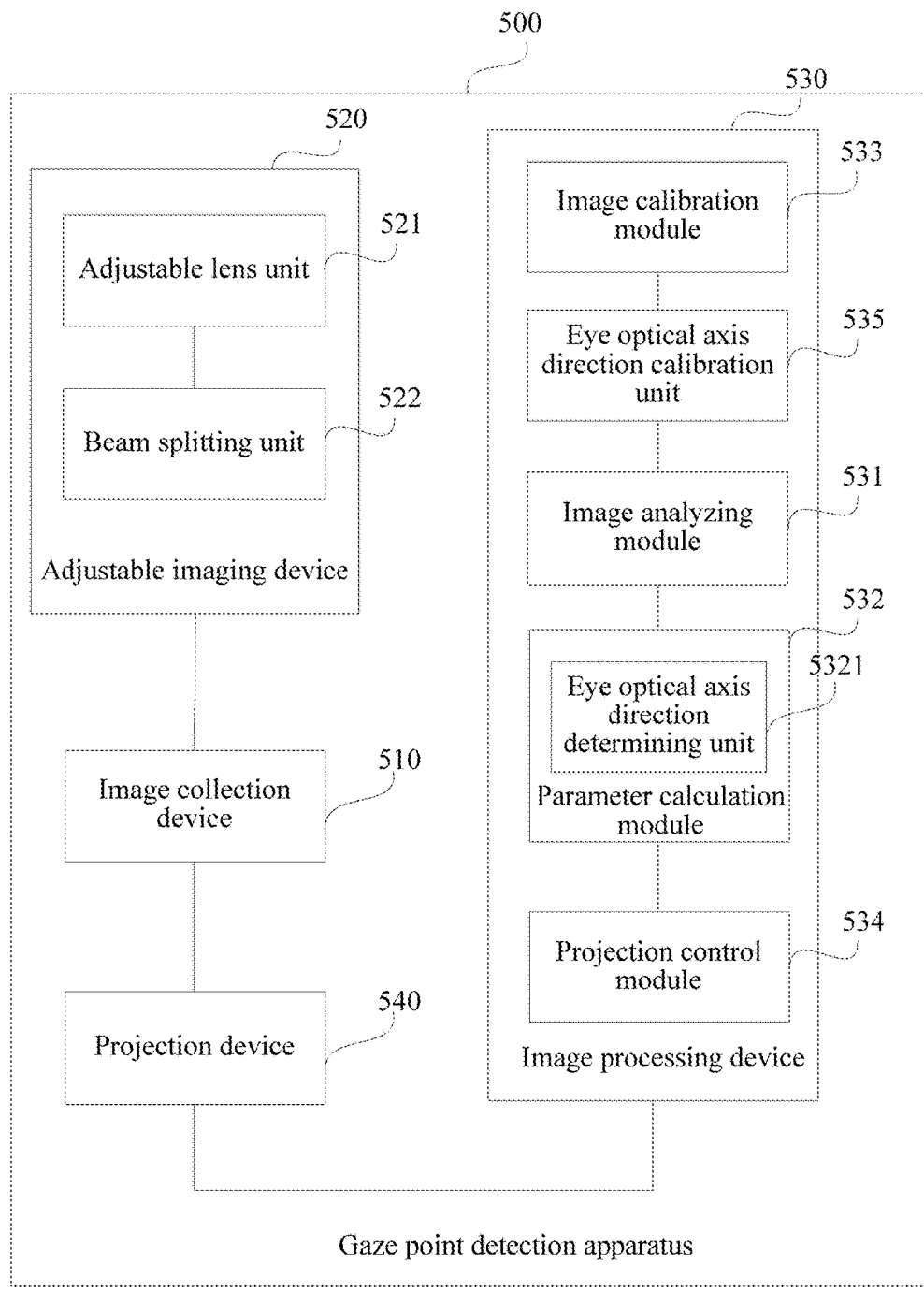
FIG. 5b is a structural block diagram of another gaze point detection apparatus of a content projection system according to an embodiment of the present application.

As shown in FIG. 5b, in a possible implementation manner of the embodiment of the present application, the image collection device 510 is a micro camera; and in another possible implementation manner of the embodiment of the present application, a light-sensitive imaging component, such as a CCD or a CMOS, may further be used as the image collection device 510 directly.

In a possible implementation manner of the embodiment of the present application, the adjustable imaging device 520 comprises: an adjustable lens unit 521, located on an optical path between the eye and the image collection device 510, where a focal length of the adjustable lens unit 521 is adjustable and/or a location of the adjustable lens unit 521 on the optical path is adjustable. With the adjustable lens unit 521, a system equivalent focal length between the eye and the image collection device 510 becomes adjustable. By means of the adjustment of the adjustable lens unit 521, the image collection device 510 obtains the clearest image of the fundus at a certain location or in a certain state of the adjustable lens unit 521. In this implementation manner, the adjustable lens unit 521 performs continuous and real-time adjustment in a detection process.

Preferably, in a possible implementation manner of the embodiment of the present application, the adjustable lens unit 521 is a focal length adjustable lens, configured to adjust the focal length of the focal length adjustable lens 521 by adjusting the refractive index and/or the shape of the focal length adjustable lens 521. Specifically: 1) the focal length is adjusted by adjusting the curvature of at least one surface of the focal length adjustable lens, for example, the curvature of the focal length adjustable lens is adjusted by adding or reducing a liquid medium in a cavity formed by two transparent layers; and 2) the focal length is adjusted by adjusting the refractive index of the focal length adjustable lens, for example, the focal length adjustable lens is filled with a specific liquid crystal medium, and an arrangement manner of the liquid crystal medium is adjusted by adjusting a voltage of an electrode corresponding to the liquid crystal medium, so as to change the refractive index of the focal length adjustable lens.

In another possible implementation manner of the embodiment of the present application, the adjustable lens unit 521 comprises: a lens assembly formed by multiple lenses, configured to adjust relative locations of the lenses in the lens assembly to adjust the focal length of the lens assembly. The lens assembly may also comprise a lens of which an imaging parameter such as the focal length is adjustable.

In addition to the foregoing two manners of changing the optical path parameter of the system by adjusting characteristics of the adjustable lens unit 521, the optical path parameter of the system may also be changed by adjusting the location of the adjustable lens unit 521 on the optical path.

Preferably, in a possible implementation manner of the embodiment of the present application, to avoid affecting user's experience of viewing an observed object, and to make the system portably applied to a wearable device, the adjustable imaging device 520 further comprises: a beam splitting unit 522, configured to form a light transmission path between the eye and the observed object and a light transmission path between the eye and the image collection device 510; in this case, the optical path can be folded, which reduces the volume of the system, and other visual experience of the user is not affected as far as possible.

Preferably, in this implementation manner, the beam splitting unit comprises: a first bean splitting unit, located between the eye and the observed object, and configured to transmit light from the observed object to the eye, and transmit light from the eye to the image collection device.

The first beam splitting unit may be a beam splitter, a beam splitting optical waveguide (comprising an optical fiber) or other proper beam splitting devices.

In a possible implementation manner of the embodiment of the present application, the image processing device 530 of the system comprises an optical path calibration module, configured to calibrate the optical path of the system, for example, align and calibrate the optical axis of the optical path, so as to ensure the measurement precision.

In a possible implementation manner of the embodiment of the present application, the image processing device 530 comprises:
- an image analyzing module 531, configured to analyze images obtained by the image collection device, to find the clearest image; and
- a parameter calculation module 532, configured to calculate an optical parameter of the eye according to the clearest image, and a known imaging parameter of the system when the clearest image is obtained.

In this implementation manner, the image collection device 510 can obtain the clearest image by using the adjustable imaging device 520; however, the clearest image needs to be found by using the image analyzing module 531; then, the optical parameter of the eye can be calculated according to the clearest image and the known optical path parameter of the system. Herein, the optical parameter of the eye may comprise the optical axis direction of the eye.

In a possible implementation manner of the embodiment of the present application, preferably, the system further comprises: a projection device 540, configured to project a light spot to the fundus. In a possible implementation manner, the function of the projection device may be implemented by means of a micro projector.

Herein, the projected light spot may have no specific pattern and be merely used for illuminating the fundus.

Figure 5C:
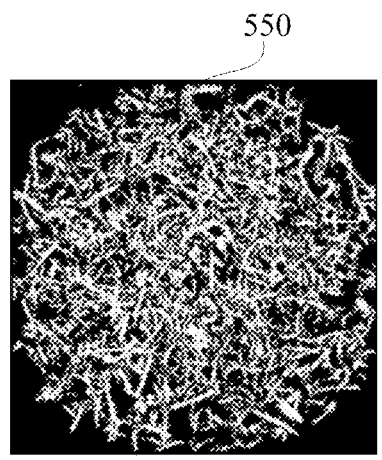
FIG. 5c is a schematic diagram of a light spot pattern used by a gaze point detection apparatus of a content projection system according to an embodiment of the present application.
Figure 5D:
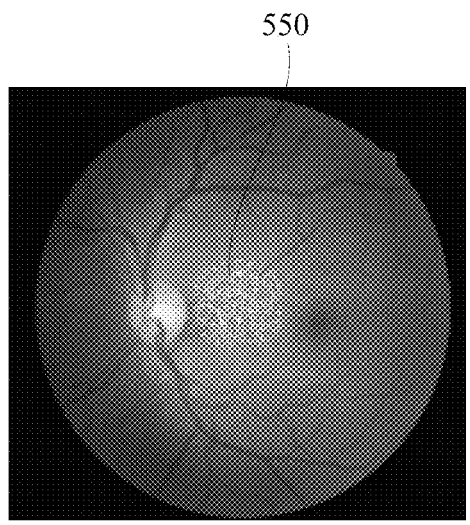
FIG. 5d is a schematic diagram of a fundus image which has a light spot pattern and is shot by a gaze point detection apparatus of a content projection system according to an embodiment of the present application.

In a preferable implementation manner of the embodiment of the present application, the projected light spot comprises a pattern with abundant features. The abundant features of the pattern facilitate detection and improve the detection precision. FIG. 5c shows an exemplary diagram of a light spot pattern 550, and the pattern can be generated by a light spot pattern generator, such as ground glass; and FIG. 5d shows an image of the fundus shot when the light spot pattern 550 is projected thereon.

In order to avoid affecting the normal viewing of the eye, preferably, the light spot is an infrared light spot invisible to the eye.

In this case, to reduce interference of other spectra:
an emergent surface of the projection device can be provided with an eye-invisible light transmission filter; and
an incident surface of the image collection device is provided with an eye-invisible light transmission filter.

Preferably, in a possible implementation manner of the embodiment of the present application, the image processing device 530 further comprises:
a projection control module 534, configured to control, according to a result obtained by the image analyzing module, the luminance of the light spot projected by the projection device.

For example, the projection control module 534 may self-adaptively adjust the luminance according to characteristics of an image obtained by the image collection device 510. Herein, the characteristics of the image comprise the contrast of image features, texture features, and the like.

Herein, a special circumstance of controlling the luminance of the light spot projected by the projection device is to turn on or turn off the projection device, for example, when the user continuously gazes at one point, the projection device can be turned off periodically; and when the fundus of the user is bright enough, a light emitting source can be turned off and a distance from the current gaze point of the sight line of the eye to the eye can be detected only using the information about the fundus.

In addition, the projection control module 534 may further control the luminance of the light spot projected by the projection device according to ambient light.

Preferably, in a possible implementation manner of the embodiment of the present application, the image processing device 530 further comprises: an image calibration module 533, configured to calibrate a fundus image to obtain at least one reference image corresponding to the image presented at the fundus.

The image analyzing module 531 compares images obtained by the image collection device 530 and the reference image, and performs calculation, to obtain the clearest image. Herein, the clearest image may be an obtained image having a minimum difference with the reference image. In this implementation manner, the difference between the currently obtained image and the reference image is calculated by using an existing image processing algorithm, for example, using a classical phase difference automatic focusing algorithm.

Preferably, in a possible implementation manner of the embodiment of the present application, the parameter calculation module 532 comprises:
an eye optical axis direction determining unit 5321, configured to obtain the optical axis direction of the eye according to features of the eye when the clearest image is obtained.

The features of the eye herein may be obtained from the clearest image, and may also be obtained otherwise. The optical axis direction of the eye indicates a gaze direction of the sight line of the eye.

Preferably, in a possible implementation manner of the embodiment of the present application, the eye optical axis direction determining unit 5321 comprises: a first determining subunit, configured to obtain the optical axis direction of the eye according to the features of the fundus when the clearest image is obtained. Compared with obtaining the optical axis direction of the eye according to the features of the pupil and the eyeball surface, the accuracy of determining the optical axis direction of the eye according to the features of the fundus is higher.

When a light spot pattern is projected to the fundus, the size of the light spot pattern may be larger than a visible region of the fundus or smaller than a visible region of the fundus, where,
when the area of the light spot pattern is smaller than or equal to that of the visible region of the fundus, the optical axis direction of the eye may be determined by detecting the location of the light spot pattern on an image relative to the fundus by using a classical feature point matching algorithm (for example, a scale invariant feature transform (SIFT) algorithm); and
when the area of the light spot pattern is larger than or equal to that of the visible region of the fundus, the optical axis direction of the eye may determined according to the location of the light spot pattern on the obtained image relative to an original light spot pattern (obtained by using the image calibration module) so as to determine the direction of the sight line of the user.

In another possible implementation manner of the embodiment of the present application, the eye optical axis direction determining unit 5321 comprises: a second determining subunit, configured to obtain the optical axis direction of the eye according to the features of the pupil of the eye when the clearest image is obtained. Herein, the features of the pupil of the eye may be obtained from the clearest image, and may also be obtained otherwise. Obtaining the optical axis direction of the eye according to the features of the pupil of the eye is an existing technology, and is not described herein again.

Preferably, in a possible implementation manner of the embodiment of the present application, the image processing device 530 further comprises: an eye optical axis direction calibration module 535, configured calibrate the optical axis direction of the eye, so as to determine the optical axis direction of the eye more accurately.

In this implementation manner, the known imaging parameter of the system comprises a fixed imaging parameter and a real-time imaging parameter, where the real-time imaging parameter is parameter information about the adjustable lens unit when the clearest image is obtained, and the parameter information may be recorded in real time when the clearest image is obtained.

Figure 5E:
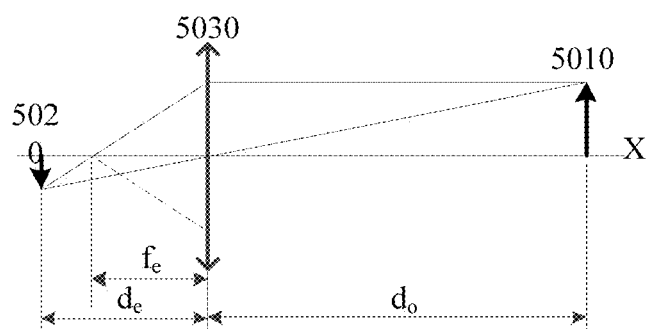
FIG. 5e is a schematic diagram of an optical path for forming an image in an eye by a gaze point detection apparatus of a content projection system according to an embodiment of the present application.

After the current optical parameter of the eye is obtained, a distance between the gaze point of the eye and the eye can be calculated, which is specifically as follows:

FIG. 5e is a schematic diagram of eye imaging; with reference to the lens imaging formula in the classical optics theory, a formula (1) can be obtained according to FIG. 5e:

$$\frac{1}{d_o} + \frac{1}{d_e} = \frac{1}{f_e} \qquad (1)$$

where $d_o$ and $d_e$ are a distance from a currently observed object 5010 of the eye to the eye and a distance from a real image 5020 on the retina to an eye equivalent lens 5030 respectively, $f_e$ is an equivalent focal length of the eye equivalent lens 5030, and X is the direction of the sight line of the eye (which can be obtained according to the optical axis direction of the eye).

Figure 5F:
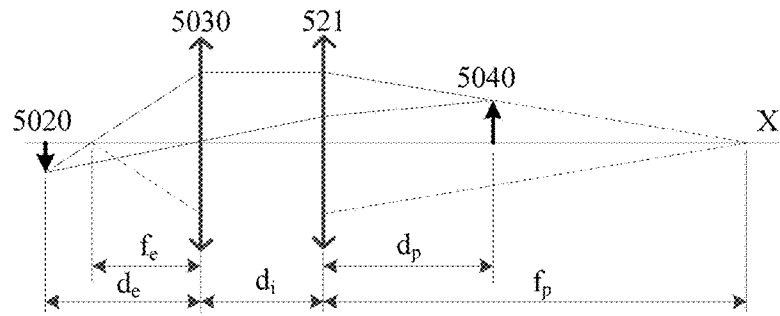
FIG. 5f is a schematic diagram of an eye gaze point location obtained according to a known imaging parameter of the system and an optical parameter of the eye by a gaze point detection apparatus of a content projection system according to an embodiment of the present application.

FIG. 5f shows a schematic diagram where a distance from a gaze point of an eye to the eye is obtained according to the known optical parameter of the system and the optical parameter of the eye, and a light spot 5040 in FIG. 5f may form a virtual image (not shown in FIG. 5f) by using the adjustable lens unit 521; assuming that a distance from the virtual image to the lens is x (not shown in FIG. 5f), the following set of equations may be obtained with reference to formula (1):

$$\begin{cases} \dfrac{1}{d_p} - \dfrac{1}{x} = \dfrac{1}{f_p} \\ \dfrac{1}{d_i + x} + \dfrac{1}{d_e} = \dfrac{1}{f_e} \end{cases} \quad (2)$$

where $d_p$ is an optical equivalent distance from the light spot 5040 to the adjustable lens unit 521, $d_i$ is an optical equivalent distance from the adjustable lens unit 521 to the eye equivalent lens 5030, $f_p$ is a focal length value of the adjustable lens unit 521, and $d_i$ is a distance from the eye equivalent lens 5030 to the adjustable lens unit 521.

According to (1) and (2), the distance $d_o$ from the currently observed object 5010 (the gaze point of the eye) to the eye equivalent lens 5030 can be obtained as shown in formula (3):

$$d_o = d_i + \dfrac{d_p \cdot f_p}{f_p - d_p} \quad (30)$$

According to the distance from the observed object 5010 to the eye obtained by the calculation described above, and the optical axis direction of the eye which can be obtained as a result of the above description, the gaze point location of the eye can be easily obtained, providing a basis for subsequent further interaction associated with the eye.

Figure 6:
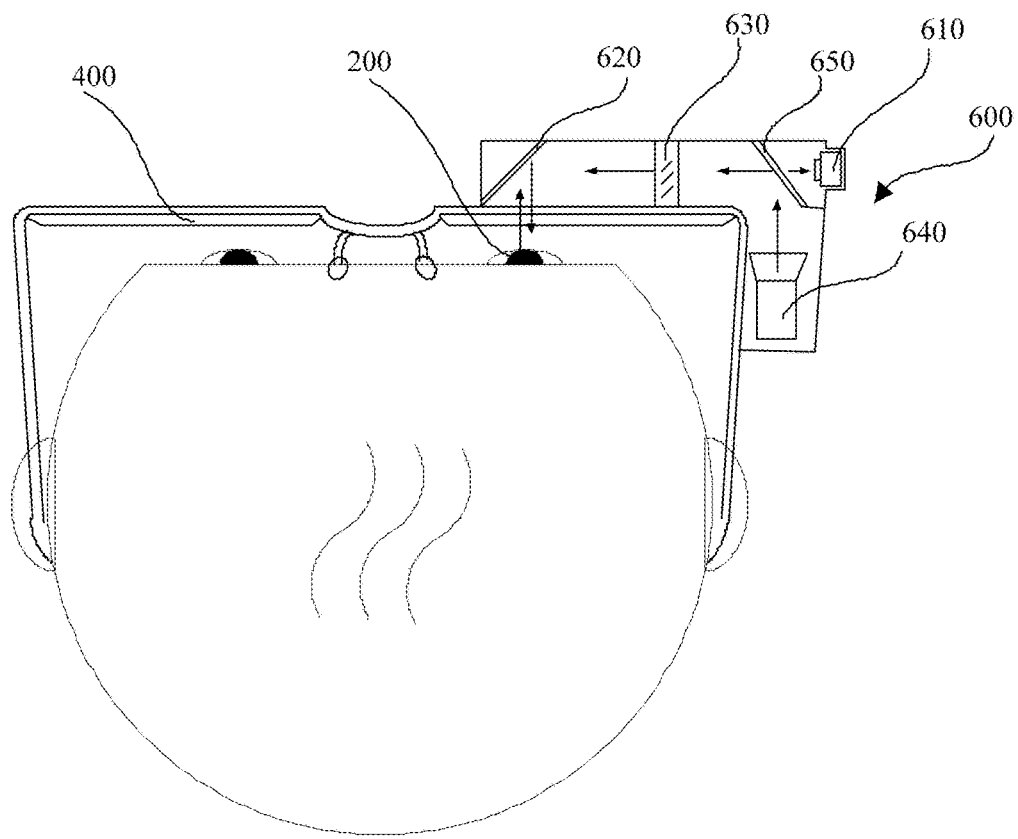
FIG. 6 is a schematic diagram of a content projection system applied to glasses according to an embodiment of the present application.

FIG. 6 shows an embodiment of applying an eye gaze point detection apparatus 600 in a possible implementation manner of the embodiment of the present application to glasses 400, which comprises the content described in the implementation manner shown in FIG. 5b, and is specifically as follows: it can be seen from FIG. 6 that, in this implementation manner, a system 600 of this implementation manner is integrated to the right side of the glasses 400 (the present application is not limited thereto), and the system 600 comprises:

a micro camera 610 which functions the same as the image collection device described in the implementation manner in FIG. 5b, and is located at the outer right side of the glasses 400 so as to avoid affecting the sight line of a user normally viewing an object;

a first beam splitter 620, which functions the same as the first beam splitting unit described in the implementation manner in FIG. 5b, is arranged with a certain tilt angle at an intersection point between a gaze direction of the eye 200 and an incident direction of the camera 610, and transmits light entering the eye 200 from an observed object and reflects light from the eye to the camera 610; and a focal length adjustable lens 630, which functions the same as the focal length adjustable lens described in the implementation manner in FIG. 5b, is located between the first beam splitter 620 and the camera 610, and adjusts the focal length value in real time, so that the camera 610 can shoot a clearest image of the fundus at a certain focal length value.

In this implementation manner, the image processing device is not shown in FIG. 6, and functions of the image processing device are the same as the image processing device shown in FIG. 5b.

Because the fundus is not bright enough under normal circumstances, it is better to illuminate the fundus; in this implementation manner, the fundus is illuminated by a light emitting source 640. In order avoid affecting user experience, preferably, the light emitting source 640 herein is an eye-invisible light emitting source, and is preferably a near-infrared light emitting source which has little impact on the eye 200 and to which the camera 610 is relatively sensitive.

In this implementation manner, the light emitting source 640 is located at an outer side of a spectacle frame on the right; therefore, a second beam splitter 650 together with the first beam splitter 620 is needed to complete the transmission of light emitted by the light emitting source 640 to the fundus. In this implementation manner, the second beam splitter 650 is also located in front of an incident surface of the camera 610, and therefore, the second beam splitter 650 further needs to transmit light from the fundus to the second beam splitter 650.

It can be seen that, in this implementation manner, to improve user experience and the collection definition of the camera 610, the first beam splitter 620 can preferably have characteristics of high reflectivity to infrared and high transmissivity to visible light. For example, an infrared reflective film may be set at one side of the first beam splitter 620 facing towards the eye 200 to implement the foregoing characteristics.

It can be seen from FIG. 6 that, in this implementation manner, the eye gaze point detection apparatus 600 is located at one side, which is away from the eye 200, of the lens of the glasses 400, and therefore, during the calculation of the optical parameter of the eye, the lens may be considered as a part of the eye 200, and in this case, there is no need to know optical characteristics of the lens.

In other implementation manners of the embodiment of the present application, the eye gaze point detection apparatus 600 may be located at one side, which is close to the eye 200, of the lens of the glasses 400; in this case, optical characteristic parameters of the lens need to be obtained in advance, and when the distance from the gaze point to the eye is calculated, influence factors of the lens are taken into consideration.

Light emitted by the light emitting source is reflected by the second beam splitter 650, projected by the focal length adjustable lens 630, and reflected by the first beam splitter 620, then enters the eye of the user through the lens of the glasses 400, and finally reaches the retina of the fundus; and the camera 610 shoots an image of the fundus through the pupil of the eye 200 via an optical path formed by the first beam splitter 620, the focal length adjustable lens 630, and the second beam splitter 650.

In a possible implementation manner of the embodiment of the present application, because the gaze point detection apparatus and the virtual image projection apparatus may each comprise: a device having a projection function (for example, the projection module of the virtual image projection apparatus and the projection device of the gaze point detection apparatus that are described above); and an imaging device with an adjustable imaging parameter (for example, the adjustable imaging module of the virtual image projection apparatus and the adjustable imaging device of the gaze point detection apparatus that are described above), the functions of the gaze point detection apparatus and the virtual image projection apparatus may be implemented by a same device.

As shown in FIG. 6, in a possible implementation manner of the embodiment of the present application, besides being used for illuminating the gaze point detection apparatus, the light emitting source 640 may further be used as a light source of the projection device of the virtual image projection apparatus to assist projecting the virtual image. In a possible implementation manner, the light emitting source 640 may simultaneously project invisible light for illuminating the gaze point detection apparatus and visible light for assisting projecting the virtual image; in another possible implementation manner, the light emitting source 640 may further project the invisible and visible light in an alternating manner at different times; and in still another possible implementation manner, the gaze point detection apparatus may implement the function of illuminating the fundus by using the virtual image.

In a possible implementation manner of the embodiment of the present application, besides being used as adjustable imaging modules of the virtual image projection apparatus, the first beam splitter 620, the second beam splitter 650, and the focal length adjustable lens 630 may further be used as adjustable imaging devices of the gaze point detection apparatus. Herein, in a possible implementation manner, the focal length of the focal length adjustable lens 630 can be adjusted in different ranges, different ranges are separately corresponding to the gaze point detection apparatus and the virtual image projection apparatus, and the focal length may also be different. Alternatively, the focal length of the focal length adjustable lens 630 is adjusted in an integrated manner, but other optical components are further disposed at the front end of a photosensitive unit (such as a CCD) of the micro camera 610 of the gaze point detection apparatus, and are configured to perform auxiliary adjustment on the imaging parameter of the gaze point detection apparatus. In addition, in another possible implementation manner, configuration is performed such that an optical path from a light emitting surface (that is, a location for projecting the virtual image) of the light emitting source 640 to the eye is the same as an optical path from the eye to the micro camera 610, and when the micro camera 610 receives a clearest fundus image through the adjustment of the focal length adjustable lens 630, the virtual image projected by the light emitting source 640 is clearly presented right at the fundus. It can be seen from the above that, the eye gaze point detection apparatus and the virtual image projection apparatus in the embodiment of the present application may be implemented by using a set of devices, so that the whole system is simple in structure, small in volume, and portable.

Figure 7:
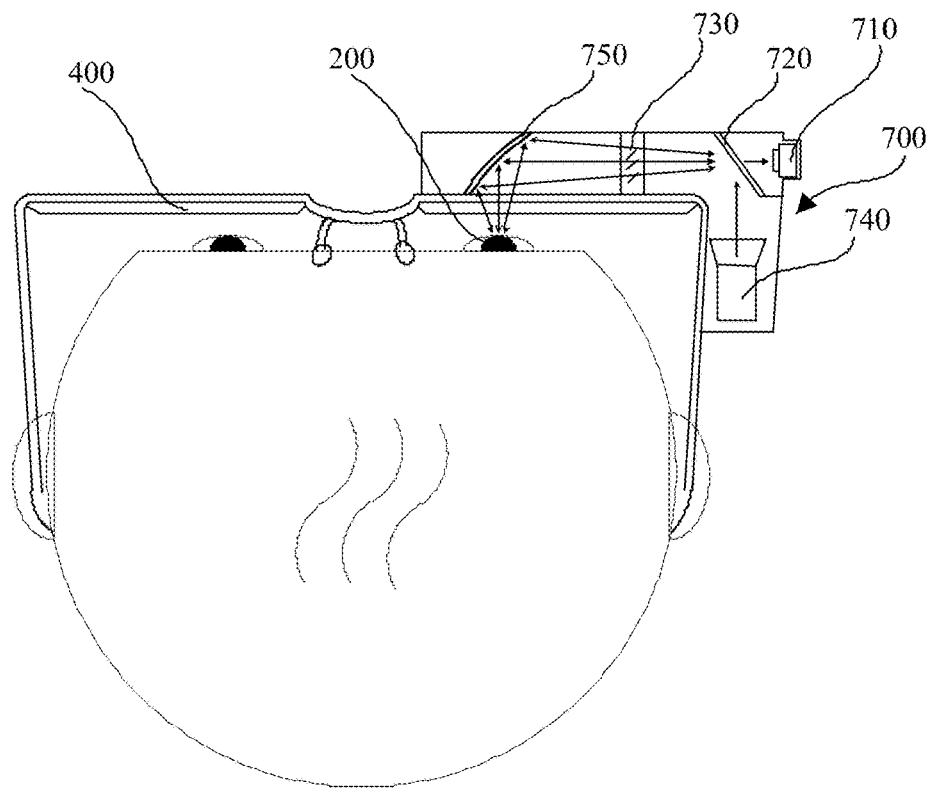
FIG. 7 is a schematic diagram of another content projection system applied to glasses according to an embodiment of the present application.

FIG. 7 is a schematic structural diagram of an eye gaze point detection apparatus 700 according to another implementation manner of an embodiment of the present application. It can be seen from FIG. 7 that, this implementation manner is similar to the implementation manner in FIG. 6, which comprises a micro camera 710, a second beam splitter 720, and a focal length adjustable lens 730, and a difference lies in that, a projection device 740 in this implementation manner is a projection device 740 for projecting a light spot pattern, and the first splitter in the implementation manner in FIG. 6 is replaced with a curved surface beam splitter 750 used as a curved-surface beam splitting unit.

Herein, the curved surface beam splitter 750 is configured to separately correspond to locations of the pupil associated with different optical axis directions of the eye and transmit an image presented at the fundus to an image collection device. In this way, a camera can shoot mixed and superposed images of various angles of the eyeball; however, because only a fundus part passing through the pupil can form a clear image on the camera, while other parts may be out of focus and cannot be clearly imaged, the imaging of the fundus part will not be interfered severely, and features of the fundus part can still be detected. Therefore, compared with the implementation manner shown in FIG. 6, in this implementation manner, an image of the fundus can be properly obtained when the gaze direction of the eye is different, so that the eye gaze point detection apparatus in the implementation manner has a wider application range and higher detection precision.

In a possible implementation manner of the embodiment of the present application, the gaze point detection apparatus and the virtual image projection apparatus may also be reused. Similar to the embodiment shown in FIG. 6, the projection device 740 may project a light spot pattern and the virtual image simultaneously or in an alternating manner at different times; or the gaze point detection apparatus uses the projected virtual image as the light spot pattern for detection. Similar to the embodiment shown in FIG. 6, in a possible implementation manner of the embodiment of the present application, besides being used as adjustable imaging modules of the virtual image projection apparatus, the first beam splitter 720, the second beam splitter 750, and the focal length adjustable lens 730 may further be used as adjustable imaging devices of the gaze point detection apparatus.

In this case, the second beam splitter 750 is further configured to perform optical path transmission between the projection module and the fundus separately corresponding to the locations of the pupil associated with different optical axis directions of the eye. Because the virtual image projected by the projection device 740 is deformed after passing through the curved second beam splitter 750, in this implementation manner, the virtual image projection apparatus comprises:

a reverse deformation processing module, configured to perform, on the virtual image, reverse deformation processing corresponding to the curved-surface beam splitting unit, so that the fundus receives the virtual image needing to be presented.

In a possible implementation manner of the embodiment of the present application, to implement three-dimensional display, the visual information is separately corresponding to two eyes of the user.

In a possible implementation manner, the visual information corresponding to the two eyes of the user may be the same, but the imaging parameters of the visual information are separately corresponding to the two eyes of the user. For example, locations at which the same visual information separately corresponding to the two eyes needs to be presented are slightly different, and sizes of the locations may also be slightly different; in addition, because the locations of the two eyes are different, virtual camera parameters corresponding to the rendering parameter may also be slightly different. Therefore, two virtual images are generated according to the visual information separately corresponding to the two eyes and/or the imaging parameters of the visual information, and the virtual images are separately corresponding to the two eyes.

For example, a virtual image corresponding to a left eye is generated according to an imaging parameter of visual information corresponding to the left eye and corresponding visual information; and a virtual image corresponding to a right eye is generated according to an imaging parameter of visual information corresponding to the right eye and corresponding visual information. When the two eyes of the user correspondingly receive the two virtual images separately, a three-dimensional visual effect will be generated.

Besides implementing projection of three-dimensional virtual content by using the foregoing method, in a possible implementation manner of the embodiment of the present application, a same virtual image is projected to the two eyes of the user, but by separately projecting the virtual image to the two eyes with a certain deviation, the three-dimensional projection can also be implemented (for example, adjusting an optical axis parameter of an adjustable imaging module in a virtual image projection apparatus).

Figure 8:
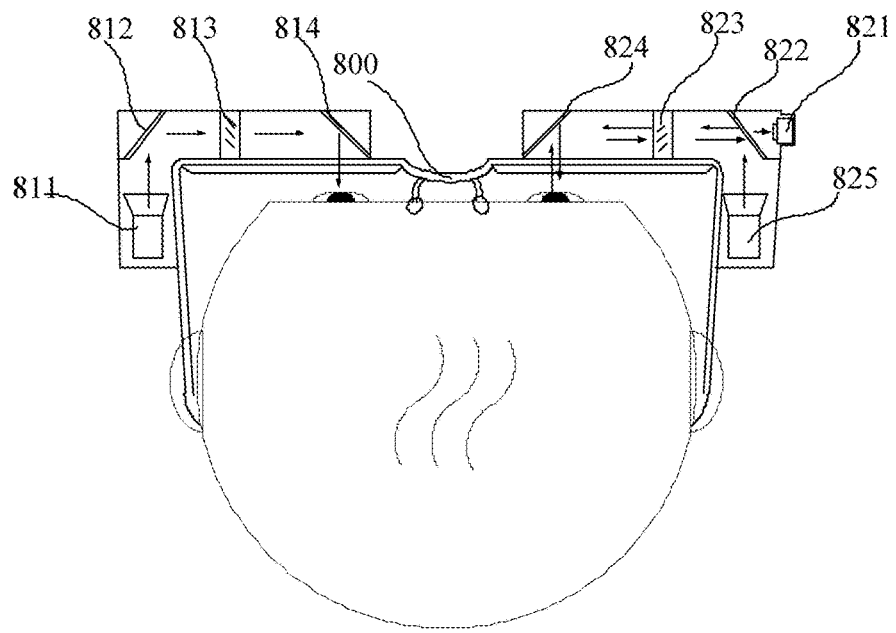
FIG. 8 is a schematic diagram of still another content projection system applied to glasses according to an embodiment of the present application.

As shown in FIG. 8, if three-dimensional display is required, the content projection system 800 needs to correspondingly set two virtual image projection apparatuses separately for two eyes of a user, comprising:

a first virtual image projection apparatus corresponding to a left eye of the user; and a second virtual image projection apparatus corresponding to a right eye of the user.

A structure of the second virtual image projection apparatus is similar to a structure integrating the functions of the gaze point detection apparatus described in the embodiment in FIG. 6, and may also be a structure which can implement both the functions of the gaze point detection apparatus and the functions of the virtual image projection apparatus, which comprises a micro camera 821, a second beam splitter 822, a second focal length adjustable lens 823, and a first beam splitter 824 (the image processing device of the gaze point detection apparatus and the imaging parameter generating module of the virtual image projection apparatus are not shown in FIG. 8) having same functions as the embodiment shown in FIG. 6, and a difference lies in that, the projection device in this implementation manner may be a second projection device 825 for projecting the virtual image corresponding to the right eye, where the second virtual image projection apparatus may be configured to detect the gaze point location of the eye of the user, and clearly project the virtual image corresponding to the right eye to the fundus of the right eye.

A structure of the first virtual image projection apparatus is similar to the structure of the second virtual image projection apparatus 820 (the imaging parameter generating module of the virtual image projection apparatus is not shown in FIG. 8), but the first virtual image projection apparatus does not have a micro camera, and does not integrate the functions of the gaze point detection apparatus. As shown in FIG. 8, the first virtual image projection apparatus comprises:

a first projection device 811, configured to project the virtual image corresponding to the left eye to the fundus of the left eye;

a first focal length adjustable lens 813, configured to adjust an imaging parameter between the first projection device 811 and the fundus, so that a corresponding virtual image can be clearly presented at the fundus of the left eye;

a third beam splitter 812, configured to perform optical path transmission between the first projection device 811 and the first focal length adjustable lens 813; and a fourth beam splitter 814, configured to perform optical path transmission between the first focal length adjustable lens 813 and the fundus of the left eye.

Figure 9:
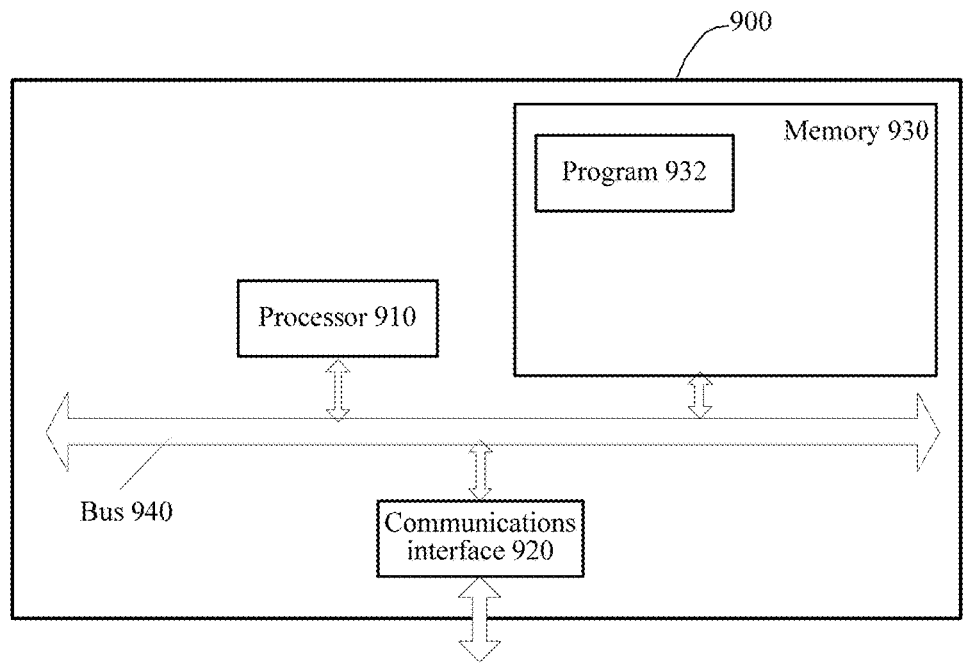
FIG. 9 is a structural block diagram of an information processing part of a content projection system according to an embodiment of the present application.

FIG. 9 is a schematic structural diagram of an information processing part 900 according to an embodiment of the present application. A specific embodiment of the present application is not intended to limit specific implementation of the information processing part 900. As shown in FIG. 9, the information processing part 900 may comprise:

a processor 910, a communications interface 920, a memory 930, and a communication bus 940, where, the processor 910, the communications interface 920, and the memory 930 complete mutual communication via the communication bus 940;

the communications interface 920 is configured to communicate with a network element such as a client; and the processor 910 is configured to execute a program 932, and can specifically execute relevant functions of the image generating apparatus, the gaze point detection apparatus, and the image processing devices of the imaging parameter generating module and the reverse deformation processing module of the virtual image projection apparatus in the apparatus embodiments shown in FIG. 1 to FIG. 8.

Specifically, the program 932 may comprise program code, and the program code comprises a computer operation instruction.

The processor 910 may be a central processing unit (CPU), or an application specific integrated circuit (ASIC), or is configured as one or more integrated circuits for implementing the embodiment of the present application.

The memory 930 is configured to store the program 932. The memory 930 may comprise a high-speed RAM memory, or may further comprise a non-volatile memory, for example, at least one magnetic memory.

It is clear to persons skilled in the art that, to make the description easy and brief, reference may be made to corresponding descriptions in the foregoing apparatus embodiments for specific operating processes of the devices and modules described above, descriptions are not repeated herein.

The foregoing content projection system according to the embodiment of the present application can automatically detect a gaze point location of a user in real time and self-adaptively process, corresponding to the gaze point location, virtual content needing to be projected, so that the virtual content and real or virtual scenarios being viewed by a user are fused with a better effect, and visual experience of the user is improved.

Figure 10:
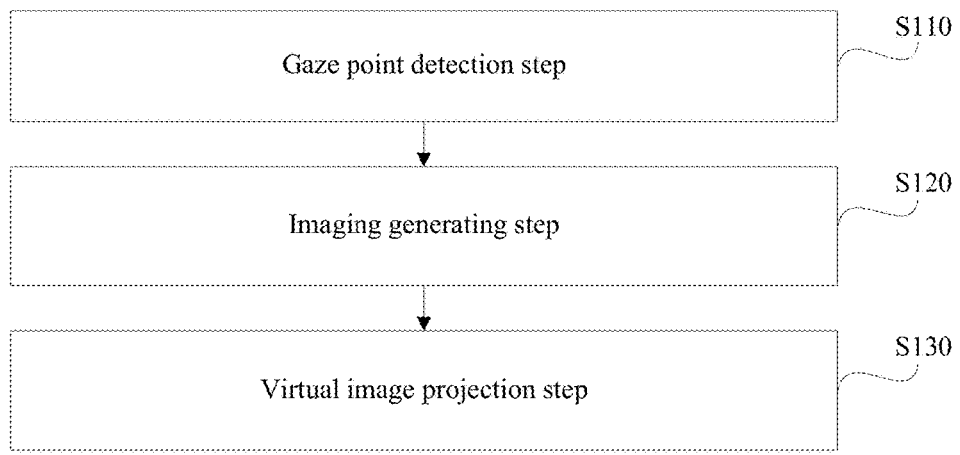
FIG. 10 is a flowchart of a content projection method according to an embodiment of the present application.

As shown in FIG. 10, a possible implementation manner of an embodiment of the present application provides a content projection method, comprising:

S110: A gaze point detection step, for detecting a current gaze point location of an eye.

S120: An image generating step, for generating a virtual image according to visual information and the gaze point location.

S130: A virtual image projection step, for projecting the virtual image to the fundus according to the gaze point location.

In the embodiment of the present application, a gaze point location of an eye is detected in real time, and a corresponding virtual image is generated according to the current gaze point location, so that a virtual image viewed by a user changes as the gaze point changes, the virtual image can be better fused with a current real scenario or virtual scenario, and the user has a more real feeling, which brings a better sense of immersion.

Preferably, in a possible implementation manner of the embodiment of the present application, the visual information comprises: graphic information and/or image information.

Preferably, in a possible implementation manner of the embodiment of the present application, the image generating step comprises:

a visual information parameter determining step, for determining an imaging parameter of the visual information according to the gaze point location.

Preferably, in a possible implementation manner of the embodiment of the present application, the image generating step further comprises:

an image rendering step, for generating, by means of rendering, the virtual image according to the visual information and the imaging parameter of the visual information.

Preferably, in a possible implementation manner of the embodiment of the present application, the visual information is separately corresponding to two eyes of the user.

Preferably, in a possible implementation manner of the embodiment of the present application, the imaging parameters of the visual information are separately corresponding to the two eyes of the user.

Preferably, in a possible implementation manner of the embodiment of the present application, the virtual image projection step comprises:

projecting the virtual image to the corresponding fundus;
generating at least one projection imaging parameter of an optical path between a projection location and the fundus according to the gaze point location; and
presenting the projected virtual image at the fundus.

Preferably, in a possible implementation manner of the embodiment of the present application, the virtual image projection step further comprises:

forming an image of the virtual image at the fundus separately corresponding to locations of a pupil associated with different optical axis directions of the eye.

Preferably, in a possible implementation manner of the embodiment of the present application, the virtual image projection step comprises:

performing, on the virtual image, reverse deformation processing corresponding to the locations of the pupil associated with different optical axis directions of the eye, so that the fundus receives the virtual image needing to be presented.

Preferably, in a possible implementation manner of the embodiment of the present application, the method further comprises:

detecting a current size of the pupil of the eye.

Preferably, in a possible implementation manner of the embodiment of the present application, the imaging parameter of the visual information comprises depth-of-field information.

Preferably, in a possible implementation manner of the embodiment of the present application, the visual information parameter determining step further comprises generating the depth-of-field information according to the size of the pupil of the eye.

Preferably, in a possible implementation manner of the embodiment of the present application, the image rendering step comprises:

performing corresponding bokeh imaging processing on the visual information according to the imaging parameter of the visual information.

Preferably, in a possible implementation manner of the embodiment of the present application, the gaze point detection step comprises:

collecting an image presented at the fundus of the eye;
adjusting an imaging parameter of an optical path between an image collection location and the eye so as to collect a clearest image; and
processing an image obtained by an image collection device, and calculating the gaze point location of the eye according to the imaging parameter of the optical path between the image collection device and the eye when the clearest image is obtained and an optical parameter of the eye.

Preferably, in a possible implementation manner of the embodiment of the present application, the adjusting an imaging parameter of an optical path between an image collection location and the eye comprises:

adjusting a focal length of a lens unit on the optical path between the eye and the image collection location and/or a location of the lens unit on the optical path.

Preferably, in a possible implementation manner of the embodiment of the present application, the gaze point detection step further comprises:

transmitting the image presented at the fundus to the image collection device separately corresponding to the locations of the pupil associated with different optical axis directions of the eye.

Preferably, in a possible implementation manner of the embodiment of the present application, the gaze point detection step further comprises:

projecting a light spot pattern to the fundus.

The implementation manners of the foregoing various steps are the same as those in the descriptions of functions of corresponding modules or units in the foregoing apparatus embodiments, and are not described herein again.

Persons skilled in the art may understand that, in the foregoing methods of the specific implementation manners of the present application, serial numbers of the steps do not mean an execution sequence. The execution sequence of the steps should be determined according to the functions and internal logic of the steps, and should not constitute any limitation on the implementation processes of the specific implementation manners of the present application.

Persons of ordinary skill in the art can understand that, units and method steps of examples described with reference to the embodiments disclosed in the present application can be implemented by electronic hardware or a combination of computer software and electronic hardware. Whether these functions are implemented in a manner of hardware or software depends on a specific application and a design constraint condition of the technical solution. Persons skilled in the art can implement the described functions for each specific application by using a different method, but such implementation shall not be considered beyond the scope of the present application.

If the functions are implemented in a form of a software function unit and are sold or used as independent products, the functions can be stored in a computer readable storage medium. Based on this, the above technical solution of the present application essentially or a part that contributes to the prior art or a part of the technical solution can be embodied in the form of a software product. The computer software product is stored in a storage medium, and comprises several instructions to instruct computer equipment (for example, a personal computer, a server, or network equipment) to perform all or a part of steps of the methods described in the embodiments of the present application. The foregoing storage medium includes: any medium that can store program code, such as a USB flash drive, a removable hard disk, a read-only memory (ROM), a random access memory (RAM), a magnetic disk, or an optical disc.

The foregoing implementation manners are merely used for explaining the present application, and are not intended to limit the present application. Persons of ordinary skill in the relevant technical field can make various changes and modifications without departing from the spirit and scope of the present application, and therefore, all equivalent technical solutions also belong to the scope of the present application. The patent protection scope of the present application shall be subject to the claims.

What is claimed is:

1. A system, comprising:
    a gaze point detection apparatus that detects a gaze point location of an eye of a user, wherein the gaze point detection apparatus comprises:
        an image collection device that collects an image presented at a fundus of the eye;
        an adjustable imaging device that adjusts an imaging parameter of an optical path between the image collection device and the eye, enabling the image collection device to obtain a clearest image; and
        an image processing device that processes the image obtained by the image collection device, and determines the gaze point location of the eye according to the imaging parameter for the clearest image obtained and an optical parameter of the eye;
    an image generating apparatus that generates a virtual image based on visual information and gaze point information comprising an indication of the gaze point location; and
    a virtual image projection apparatus that projects the virtual image to the fundus of the eye based on the gaze point information, wherein the gaze point information comprises distance information corresponding to a distance from the gaze point location to the eye of the user.

2. The system of claim 1, wherein the image generating apparatus comprises:
    a visual information parameter determining module that determines at least one imaging parameter of the visual information based on the gaze point information.

3. The system of claim 2, wherein the image generating apparatus further comprises:
    an image rendering module that renders the virtual image based on the visual information and the at least one imaging parameter of the visual information.

4. The system of claim 3, wherein the visual information corresponds to two eyes of the user.

5. The system of claim 3, wherein the at least one imaging parameter of the visual information corresponds to two eyes of the user.

6. The system of claim 3, wherein the gaze point detection apparatus further comprises:
    a pupil detection module that detects a size of a pupil of the eye.

7. The system of claim 6, wherein the at least one imaging parameter of the visual information comprises depth-of-field information; and
    wherein the visual information parameter determining module further determines the depth-of-field information based on the size of the pupil of the eye.

8. The system of claim 7, wherein the image rendering module comprises:
    a bokeh processing unit that performs corresponding bokeh imaging processing on the visual information based on the at least one imaging parameter of the visual information.

9. The system of claim 1, wherein the virtual image projection apparatus comprises:
    a projection module that projects the virtual image to the fundus of the eye;
    an adjustable imaging module, located on an optical path between the projection module and the fundus, generating, at the fundus, the virtual image projected by the projection module; and
    an imaging parameter determining module that determines at least one projection imaging parameter of the adjustable imaging module based on the gaze point information.

10. The system of claim 9, wherein the adjustable imaging module further comprises:
    a beam splitting unit that forms the optical path between the projection module and the fundus.

11. The system of claim 10, wherein the beam splitting unit comprises:
    a curved-surface beam splitting unit that forms different optical paths between the projection module and the fundus separately corresponding to different locations of a pupil associated with different optical axis directions of the eye.

12. The system of claim 11, wherein the virtual image projection apparatus comprises:
    a reverse deformation processing module that performs, on the virtual image, reverse deformation processing corresponding to the curved-surface beam splitting unit, to cause the fundus to receive the virtual image being presented.

13. The system of claim 1, wherein the adjustable imaging device comprises:
    an adjustable lens unit located on the other optical path, wherein a focal length of the adjustable lens unit is adjustable or a location of the adjustable lens unit on the other optical path is adjustable.

14. The system of claim 1, wherein the adjustable imaging device comprises:
    a curved-surface beam splitting unit that transmits the at least one image to the image collection device corresponding to different locations of the pupil associated with different optical axis directions of the eye.

15. The system of claim 1, wherein the gaze point detection apparatus further comprises:
    a projection device that projects a light spot pattern to the fundus.

16. The system of claim 1, wherein the gaze point detection apparatus and the virtual image projection apparatus are part of a same apparatus.

17. The system of claim 1, wherein the content projection system is comprised in a pair of glasses.

18. A method, comprising:
    detecting, by a system comprising a processor, a gaze point location of an eye of a user, wherein the detecting comprises:
        collecting, by an image collection device, an image presented at a fundus of the eye;
        adjusting, by an adjustable imaging device, an imaging parameter of an optical path between the image collection device and the eye, enabling the image collection device to obtain a clearest image; and determining, by an image processing device and based on the image obtained by the image collection device, the gaze point location of the eye according to the imaging parameter for the clearest image obtained and an optical parameter of the eye;

generating a virtual image based on visual information and the gaze point location; and projecting the virtual image to the fundus of the eye based on the gaze point location, wherein the gaze point location is at a determined distance from the eye of the user.

19. The method of claim 18, wherein the visual information comprises: graphic information or image information.

20. The method of claim 19, wherein the generating the virtual image comprises:

determining at least one imaging parameter of the visual information based on the gaze point location and the determined distance.

21. The method of claim 20, wherein the generating the virtual image further comprises:

rendering the virtual image based on the visual information and the at least one imaging parameter of the visual information.

22. The method of claim 21, wherein the visual information corresponds to two eyes of the user.

23. The method of claim 21, wherein the at least one imaging parameter of the visual information corresponds to two eyes of the user.

24. The method of claim 19, further comprising:
detecting a size of a pupil of the eye.

25. The method of claim 18, wherein the projecting the virtual image to the fundus comprises:

projecting the virtual image to the fundus of the eye;

determining at least one projection imaging parameter of an optical path between a projection location and the fundus based on the gaze point location and the determined distance; and imaging, at the fundus, the virtual image projected.

26. The method of claim 25, wherein the projecting the virtual image to the fundus further comprises:

imaging the virtual image at the fundus separately corresponding to different locations of a pupil associated with different optical axis directions of the eye.

27. The method of claim 26, wherein the projecting the virtual image to the fundus comprises:

performing, on the virtual image, reverse deformation processing corresponding to the locations of the pupil associated with different optical axis directions of the eye, to cause the fundus to receive the virtual image to be presented.

28. The method of claim 26, wherein the at least one imaging parameter of the visual information comprises depth-of-field information.

29. The method of claim 28, wherein determining the at least one imaging parameter further comprises:

determining the depth-of-field information based on a size of the pupil of the eye.

30. The method of claim 29, wherein the generating the virtual image comprises:

performing corresponding bokeh imaging processing on the visual information based on the at least one imaging parameter of the visual information.

31. The method of claim 18, wherein the adjusting the at least one other imaging parameter comprises: adjusting a location of a lens unit on the other optical path or a focal length of the lens unit.

32. The method of claim 18, wherein the detecting the gaze point location further comprises: transmitting the at least one image presented at the fundus to the image collection location separately corresponding to different locations of a pupil when an optical axis of the eye is in different directions.

33. The method of claim 18, wherein detecting the gaze point location further comprises: projecting a light spot pattern to the fundus.

34. A computer readable storage device comprising executable instructions that, in response to execution, cause a system comprising a processor to perform operations, comprising:

determining a gaze point location of an eye of a user, wherein the determining comprises:

collecting, by an image collection device, an image presented at a fundus of the eye;

adjusting, by an adjustable imaging device, an imaging parameter of an optical path between the image collection device and the eye, enabling the image collection device to obtain a clearest image; and determining, by an image processing device and based on the image obtained by the image collection device, the gaze point location of the eye according to the imaging parameter for the clearest image obtained and an optical parameter of the eye;

generating a virtual image based on visual information and the gaze point location; and rendering the virtual image to the fundus of the eye based on the gaze point location and a distance between the gaze point location and the eye of the user.

35. The computer readable storage device of claim 34, wherein the generating a virtual image comprises:

determining at least one imaging parameter of the visual information based on the gaze point information.

36. The computer readable storage device of claim 35, wherein the generating a virtual image further comprises:

rendering the virtual image based on the visual information and the at least one imaging parameter of the visual information.

* * * * *